(12) United States Patent
Victor

(10) Patent No.: US 11,744,647 B2
(45) Date of Patent: Sep. 5, 2023

(54) WIRELESS MEDICAL DEVICE NAVIGATION SYSTEMS AND METHODS

(71) Applicant: TELEFLEX MEDICAL INCORPORATED, Morrisville, NC (US)

(72) Inventor: John C. Victor, Kunkletown, PA (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 249 days.

(21) Appl. No.: 16/760,640

(22) PCT Filed: Nov. 8, 2018

(86) PCT No.: PCT/US2018/059727
§ 371 (c)(1),
(2) Date: Apr. 30, 2020

(87) PCT Pub. No.: WO2019/094530
PCT Pub. Date: May 16, 2019

(65) Prior Publication Data
US 2020/0345427 A1 Nov. 5, 2020

Related U.S. Application Data

(60) Provisional application No. 62/583,315, filed on Nov. 8, 2017.

(51) Int. Cl.
*A61B 34/20* (2016.01)
*A61B 17/00* (2006.01)

(52) U.S. Cl.
CPC .... *A61B 34/20* (2016.02); *A61B 2017/00221* (2013.01); *A61B 2034/2051* (2016.02)

(58) Field of Classification Search
CPC .......... A61B 34/20; A61B 2017/00221; A61B 2034/2051; H02J 50/20; G01C 21/00
See application file for complete search history.

(56) References Cited

U.S. PATENT DOCUMENTS

| | | | |
|---|---|---|---|
| 3,775,765 | A | 11/1973 | Di Piazza et al. |
| 4,173,228 | A | 11/1979 | Van Steenwyk et al. |
| (Continued) | | | |

FOREIGN PATENT DOCUMENTS

| | | |
|---|---|---|
| AU | 2012258469 A1 | 12/2012 |
| CN | 1911171 A | 2/2007 |
| (Continued) | | |

OTHER PUBLICATIONS

International Search Report from PCT/US2018/059727; dated Dec. 18, 2018.
(Continued)

*Primary Examiner* — Jermele M Hollington
*Assistant Examiner* — Suresh K Rajaputra
(74) *Attorney, Agent, or Firm* — BakerHostetler

(57) ABSTRACT

The present disclosure relates to a navigation system for placing a medical device into a patient. The system may include an external unit configured to be disposed on a chest of the patient, the external unit having: a radiating element configured to produce a first radio frequency ("RF") signal; and a plurality of three-axis sensors configured to receive a second RF signal. The system may also include a medical device such as a catheter. The catheter may have: a first antenna configured to receive the first RF signal and produce an alternating current; a rectifier configured to convert the alternating current into a direct current; a frequency generator configured to produce a second RF signal that is received by the plurality of three-axis sensors. The RF signals received by the plurality of three-axis sensors may be used
(Continued)

to determine a position of the catheter relative to the external unit.

20 Claims, 8 Drawing Sheets

(56) References Cited

U.S. PATENT DOCUMENTS

| | | | |
|---|---|---|---|
| 4,560,930 A | 12/1985 | Kouno | |
| 4,959,613 A | 9/1990 | Yamamoto et al. | |
| 5,005,592 A | 4/1991 | Cartmell | |
| 5,099,845 A | 3/1992 | Besz et al. | |
| 5,307,072 A | 4/1994 | Jones, Jr. | |
| 5,377,678 A | 1/1995 | Dumoulin et al. | |
| 5,425,367 A | 6/1995 | Shapiro et al. | |
| 5,429,132 A | 7/1995 | Guy et al. | |
| 5,558,091 A | 9/1996 | Acker et al. | |
| 5,645,065 A | 7/1997 | Shapiro et al. | |
| 5,729,129 A | 3/1998 | Acker | |
| 5,769,843 A | 6/1998 | Abela et al. | |
| 5,879,297 A | 3/1999 | Haynor et al. | |
| 5,913,820 A | 6/1999 | Bladen et al. | |
| 5,997,473 A | 12/1999 | Taniguchi et al. | |
| 6,073,043 A | 6/2000 | Schneider | |
| 6,161,032 A * | 12/2000 | Acker | A61B 5/06 324/207.11 |
| 6,474,341 B1 | 11/2002 | Hunter et al. | |
| 6,484,118 B1 | 11/2002 | Govari | |
| 6,487,516 B1 | 11/2002 | Amorai-Moriya | |
| 6,516,212 B1 | 2/2003 | Bladen et al. | |
| 6,522,907 B1 | 2/2003 | Bladen et al. | |
| 6,534,982 B1 | 3/2003 | Jakab | |
| 6,615,155 B2 | 9/2003 | Gilboa | |
| 6,677,755 B2 | 1/2004 | Belt et al. | |
| 6,690,963 B2 | 2/2004 | Ben-Haim et al. | |
| 6,701,179 B1 | 3/2004 | Martinelli et al. | |
| 6,755,789 B2 | 6/2004 | Stringer et al. | |
| 6,757,557 B1 | 6/2004 | Bladen et al. | |
| 6,774,624 B2 | 8/2004 | Anderson et al. | |
| 7,048,716 B1 | 5/2006 | Kucharczyk et al. | |
| 7,152,608 B2 | 12/2006 | Hunter et al. | |
| 7,173,228 B2 | 2/2007 | Benthien | |
| 7,174,202 B2 | 2/2007 | Bladen et al. | |
| 7,214,191 B2 | 5/2007 | Stringer et al. | |
| 7,366,562 B2 | 4/2008 | Dukesherer et al. | |
| 7,643,848 B2 | 1/2010 | Robinett | |
| 7,729,742 B2 | 6/2010 | Govari | |
| 7,806,828 B2 | 10/2010 | Stringer | |
| 7,819,810 B2 | 10/2010 | Stringer et al. | |
| 8,095,330 B2 | 1/2012 | Kimura et al. | |
| 8,197,494 B2 | 6/2012 | Jaggi et al. | |
| 8,369,930 B2 | 2/2013 | Jenkins et al. | |
| 8,380,289 B2 | 2/2013 | Zellers et al. | |
| 8,388,541 B2 | 3/2013 | Messerly et al. | |
| 8,391,956 B2 | 3/2013 | Zellers et al. | |
| 8,849,382 B2 | 9/2014 | Cox et al. | |
| 9,636,031 B2 | 5/2017 | Cox | |
| 9,649,048 B2 | 5/2017 | Cox et al. | |
| 9,999,371 B2 | 6/2018 | Messerly et al. | |
| 10,098,567 B2 | 10/2018 | Nelson et al. | |
| 10,165,962 B2 | 1/2019 | Messerly et al. | |
| 10,197,518 B2 | 2/2019 | Nelson et al. | |
| 10,480,959 B2 | 11/2019 | Nelson et al. | |
| 11,122,991 B2 | 9/2021 | Nelson et al. | |
| 11,150,207 B2 | 10/2021 | Nelson et al. | |
| 2002/0065455 A1 | 5/2002 | Ben-Haim et al. | |
| 2003/0120150 A1* | 6/2003 | Govari | A61B 5/062 600/424 |
| 2005/0104776 A1* | 5/2005 | Anderson | A61B 34/20 342/450 |
| 2006/0058695 A1 | 3/2006 | Chen | |
| 2006/0095066 A1* | 5/2006 | Chang | A61M 25/10 606/199 |
| 2006/0293593 A1 | 12/2006 | Govari et al. | |
| 2007/0013540 A1* | 1/2007 | Altmann | A61B 34/20 340/8.1 |
| 2007/0167722 A1 | 7/2007 | Bladen et al. | |
| 2008/0077007 A1 | 3/2008 | Hastings et al. | |
| 2009/0029754 A1 | 1/2009 | Slocum et al. | |
| 2009/0281419 A1 | 11/2009 | Troesken et al. | |
| 2009/0299174 A1 | 12/2009 | Wright et al. | |
| 2010/0156399 A1 | 6/2010 | Chiba et al. | |
| 2010/0210939 A1 | 8/2010 | Hartmann et al. | |
| 2010/0219825 A1 | 9/2010 | Sato et al. | |
| 2010/0317962 A1 | 12/2010 | Jenkins et al. | |
| 2011/0166446 A1 | 7/2011 | Whitmore et al. | |
| 2012/0126808 A1 | 5/2012 | Knopp et al. | |
| 2012/0130228 A1 | 5/2012 | Zellers et al. | |
| 2012/0130229 A1 | 5/2012 | Zellers et al. | |
| 2012/0226148 A1 | 9/2012 | Jaggi et al. | |
| 2013/0303945 A1 | 11/2013 | Blumenkranz et al. | |
| 2014/0051983 A1 | 2/2014 | Schroeder et al. | |
| 2014/0139223 A1 | 5/2014 | Olsson et al. | |
| 2014/0306698 A1 | 10/2014 | Bontus et al. | |
| 2016/0245670 A1 | 8/2016 | Nelson et al. | |
| 2016/0245766 A1* | 8/2016 | Nelson | G01N 27/023 |
| 2016/0320210 A1 | 11/2016 | Nelson et al. | |
| 2016/0380488 A1 | 12/2016 | Widmer et al. | |
| 2017/0127974 A1 | 5/2017 | Bonyak et al. | |
| 2017/0281029 A1 | 10/2017 | Messerly et al. | |
| 2018/0296122 A1 | 10/2018 | Messerly et al. | |
| 2019/0086349 A1 | 3/2019 | Nelson et al. | |
| 2019/0150784 A1 | 5/2019 | Nelson et al. | |
| 2020/0085343 A1 | 3/2020 | Nelson et al. | |

FOREIGN PATENT DOCUMENTS

| | | |
|---|---|---|
| CN | 103379853 A | 10/2013 |
| EP | 1321097 A2 | 6/2003 |
| WO | 2012/068365 A2 | 5/2012 |
| WO | 2012/088535 A1 | 6/2012 |
| WO | 2016/134297 A1 | 8/2016 |
| WO | 2016/176539 A1 | 11/2016 |

OTHER PUBLICATIONS

Schneider, M., "Electromagnetic Tracking for Catheter Localization," Part of the SPIE Conference on Biomedical Diagnostic, Guidance, and Surgical-Assist Systems; San Jose, California; SPIE; vol. 3595; pp. 61-68; Jan. 1999.

Solomon, S. et al., "TIPS placement in swine, guided by electromagnetic real-time needle tip localization displayed on previously acquired 3-D CT," Cardiovascular and Interventional Radiology; vol. 22, No. 5; pp. 411-414; Sep. 1999.

International Preliminary Report on Patentability and Written Opinion issued in PCT/US2018/059727, dated May 22, 2020.

* cited by examiner

WIRELESS MEDICAL DEVICE NAVIGATION SYSTEMS AND METHODS

PRIORITY

This application is a National Stage Entry of PCT/US2018/059727 filed on Nov. 8, 2018, which claims priority to U.S. Provisional Patent Application No. 62/583,315 filed on Nov. 8, 2017, the entire disclosures of which are expressly incorporated herein by reference.

TECHNICAL FIELD

This application relates generally to systems and methods for placing a medical device within a vasculature of a patient, and more specifically to wireless medical device navigation systems disposed within a tip of a catheter.

BACKGROUND ART

A catheter is a medical device generally having a rigid or flexible tubular portion which can be placed within the vasculature of a patient to detect and treat various health issues. A catheter may be placed into a patient via openings into veins, arteries, or other internal body spaces. Cardiac catheters, including central venous catheters ("CVCs"), peripherally inserted central catheters ("PICCs"), hemodialysis ("HD") catheters, and jugular axillo-subclavian central catheters ("JACC"), require distal tip placement at a critical position within a patient's vasculature.

The correct placement of a cardiac catheter, such as a CVC, is important for many reasons. For example, in the case of an infusion catheter, correct placement allows medications to be targeted to, or for, specific areas of the body. The catheter may need to be located sufficiently near the heart in a particular region where there is a particular blood flow rate (e.g., a high flow rate) to ensure adequate dilution or mixing of infused fluids. The catheter may also need to be disposed in a particular location in order to function efficiently and effectively. While cardiac catheters such as CVCs have been used for many years, determining and tracking the tips of the catheters have been problematic.

Therefore, there remains a need for a medical device navigation system that allows physicians to accurately monitor and track the location of a catheter as it navigates through a patient's vasculature, while minimizing the need for connections that breach the sterile field.

SUMMARY OF THE DISCLOSURE

The foregoing is met, to a great extent, by a navigation system having an external unit for powering and receiving signals from an internally placed medical device, such as a catheter, having an energy harvesting coil, an oscillator for generating a RF signal, and an antenna for transmitting the RF signal to sensors disposed on the external unit.

In one or more aspects, the navigation system includes: an external unit configured to be disposed on a chest of a patient, a control system connected to the external unit, and a medical device. The external unit may include: a radiating element configured to produce a first radiofrequency ("RF") signal; and a plurality of three-axis sensors, each three-axis sensor having three orthogonally arranged receiver coils configured to receive a second RF signal. The medical device may include: a first antenna configured to receive the first RF signal and produce an alternating current; a rectifier configured to convert the alternating current into a direct current; a frequency generator configured to produce a second RF signal; and a second antenna configured to broadcast the second RF signal such that the receiver coils of the plurality of three-axis sensors receive the second RF signal, wherein at least the frequency generator and the second antenna are energized by the direct current. The control system may be configured to energize the radiating element, and the radiating element may produce the first RF signal when the control system energizes the radiating element. The control system may also be configured to determine a position of the second antenna relative to the external unit based on the second RF signal received by the receiver coils of the plurality of three-axis sensors.

In some aspects, the medical device may be a catheter (e.g., a PICC). The catheter may have a flexible tubular body having a proximal end and a distal end, and a tip attached to the distal end of the flexible tubular body. The tip of the catheter may have: a first antenna configured to receive a first RF signal and produce an alternating current; a filter configured to filter the alternating current; a rectifier configured to convert the filtered alternating current into a direct current; a frequency generator configured to produce a second RF signal; an amplifier configured to amplify the second RF signal; and a second antenna configured to broadcast the second RF signal, wherein at least the frequency generator, the amplifier, and the second antenna are energized by the direct current.

In certain aspect, the external unit may be a chest plate. The chest plate may include: a radiating element configured to produce a first RF signal; and a plurality of three-axis sensors, each three-axis sensor having three orthogonally arranged receiver coils configured to receive a second RF signal, wherein the radiating element is disposed in a center portion of the chest plate, and wherein each of the plurality of three-axis sensors is disposed proximate to an outer edge of the chest plate. The chest plate may have a generally triangular configuration with the three-axis sensors positioned on the corners and/or along an outer edge of the chest plate.

In one or more aspects, a method of determining a position of a medical device in a patient may include: positioning an external unit on a chest of a patient, the external unit including a radiating element, a plurality of three-axis sensors, each three axis sensor comprising three orthogonally arranged receive coils; inserting the medical device into the patient, the medical device including a first antenna, a rectifier, a frequency generator, and a second antenna; establishing a physical sterile barrier between the medical device and the external unit and the control system; energizing, via the control system, the radiating element to produce a first RF signal and producing an alternative current; converting, with the rectifier, the alternating current into a direct current; energizing at least the frequency generator and the second antenna with the direct current; broadcasting, with the second antenna, a second RF signal to the receiver coils of the plurality of the three-axis sensors; and determining, via the control system, the position of the medical device relative to the external unit based on the second RF signal.

There are, of course, additional aspects of the disclosure that will be described below and which will form the subject matter of the claims. In this respect, before explaining at least one aspect of the disclosure in detail, it is to be understood that the disclosure is not limited in its application to the details of construction and to the arrangements of the components set forth in the following description or illustrated in the drawings. The disclosure is capable of aspects in addition to those described and of being practiced and carried out in various ways. Also, it is to be understood that the phraseology and terminology employed herein, as well as the Abstract, are for the purpose of description and should not be regarded as limiting.

As such, those skilled in the art will appreciate that the conception upon which this disclosure is based may readily be utilized as a basis for the designing of other structures, methods, and systems for carrying out the several purposes of the disclosure. It is important, therefore, that the claims be regarded as including such equivalent constructions insofar as they do not depart from the spirit and scope of the disclosure.

BRIEF DESCRIPTION OF THE DRAWINGS

In order that the disclosure may be readily understood, aspects of the disclosure are illustrated by way of examples in the accompanying drawings.

Aspects of a medical device navigation system according to aspects of the disclosure are described with reference to the drawings, in which like reference numerals refer to like parts throughout.

DETAILED DESCRIPTION

Figure 1:
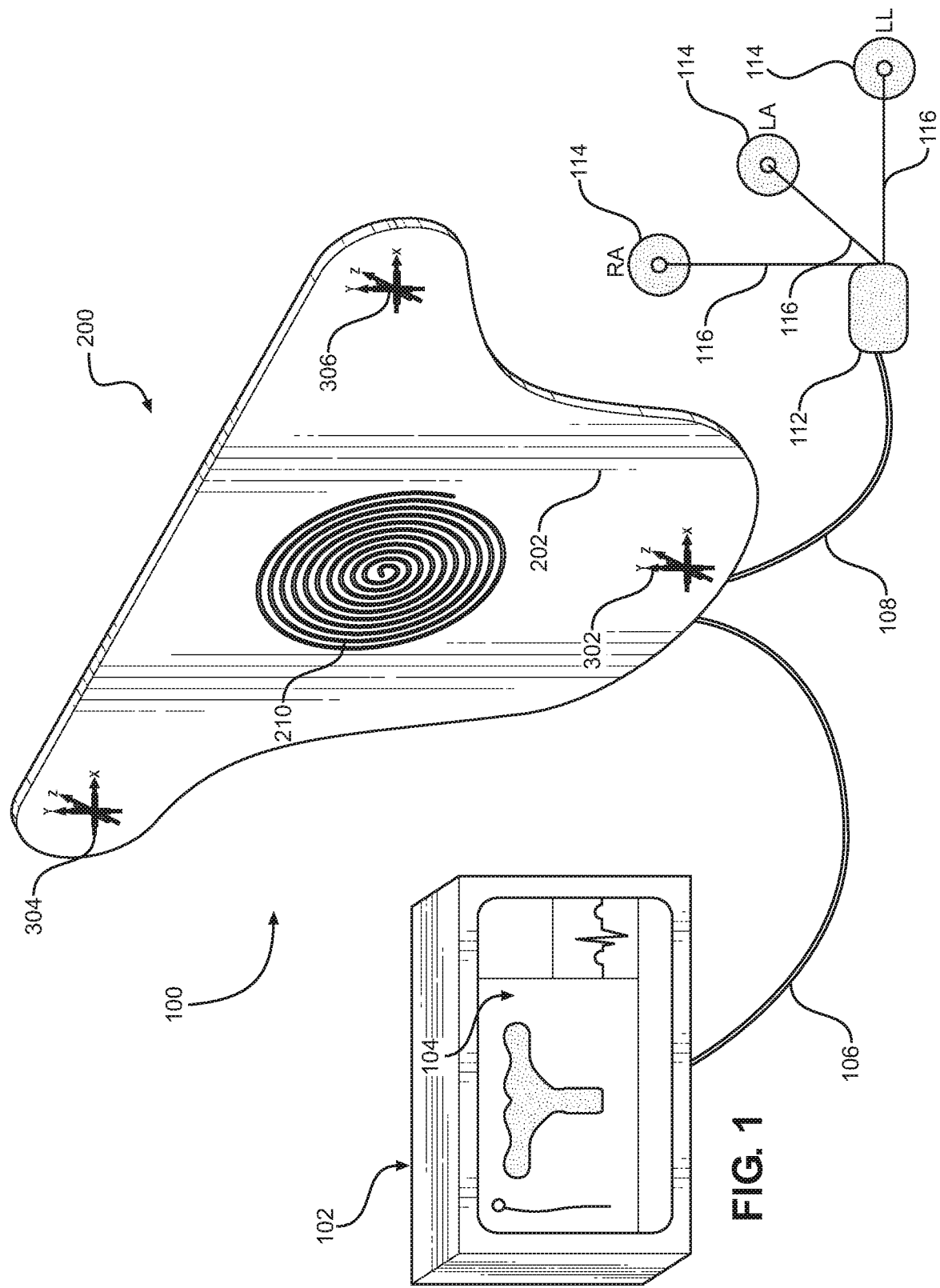
FIG. 1 depicts a schematic overview of a medical device navigation system according to aspects of the disclosure.

Systems and methods provided herein facilitate the location of a catheter without the need of a tether of conductors or some other type of wired or direct physical connection between an RF radiating antenna and an external console providing power and control to an antenna. Such systems and methods eliminate the need for a stylet with a wired or physical conductor by using energy harvesting (e.g., scavenging and/or parasitic power) to provide power and control of a radiating RF antenna located in a catheter. In some embodiments, the systems and methods may use a mechanism of energy harvesting utilizing a small RF receiver antenna tuned to a specific frequency that is generated and transmitted by an external driver antenna. These two antennas may be coupled electrically by mutual inductance, which may operate at short ranges, via a magnetic or H-field. The two antennas, along with media between them (e.g., human tissue if the radiating antenna is disposed on the skin of the patient and the receiving antenna is disposed within the patient) act as a transformer. A computer console or control system may be used to energize and pass an alternating current through the radiating or power antenna. The radiating antenna may be a coil, and the alternating current may generate a magnetic field, which then induces an alternating current within the internal harvesting antenna, which may also be a coil. The induced current and associated voltage may then be rectified and filtered to produce a source of direct current ("DC") power, which may be applied to a separate frequency generator capable of producing a signal at a specific frequency that is received by a set of external navigational antennas. These external navigational antennas may be disposed at specific locations relative to an anatomical structure of the patient.

The generated signal may be amplified by an amplifier, which may also be powered by the harvested energy from the external radiating antenna, and transmitted by an internal navigational antenna. The receiving antenna, the rectifier, the frequency generator, the amplifier, and/or the navigational antenna may also be disposed within a tip of a catheter, as further explained below with reference to FIG. 6. Advantages of the systems and methods disclosed herein, where an internal antenna is used to harvest energy via a magnetic field generated by an external antenna, include: (1) the ability to reconfirm a position of a catheter tip within the lower third of a patient's SVC (which is accommodated by the permanent residence of the internal transmitting antenna and frequency generator in the tip of a catheter as opposed to a stylet-based antenna that may need to be removed after initial catheter placement is confirmed), (2) reduced cost of materials associated with the manufacture of a stylet and connector set connecting the stylet to a console, (3) reduced need to breach a sterile field with the stylet connectivity (e.g., the wire that connects the stylet to an external console), and (4) the ability to have an embedded and permanent beacon circuit rather than a stylet, which may be used or reused in other devices even when such use is discouraged, for example, due to accuracy and cleanliness concerns.

Figure 5:
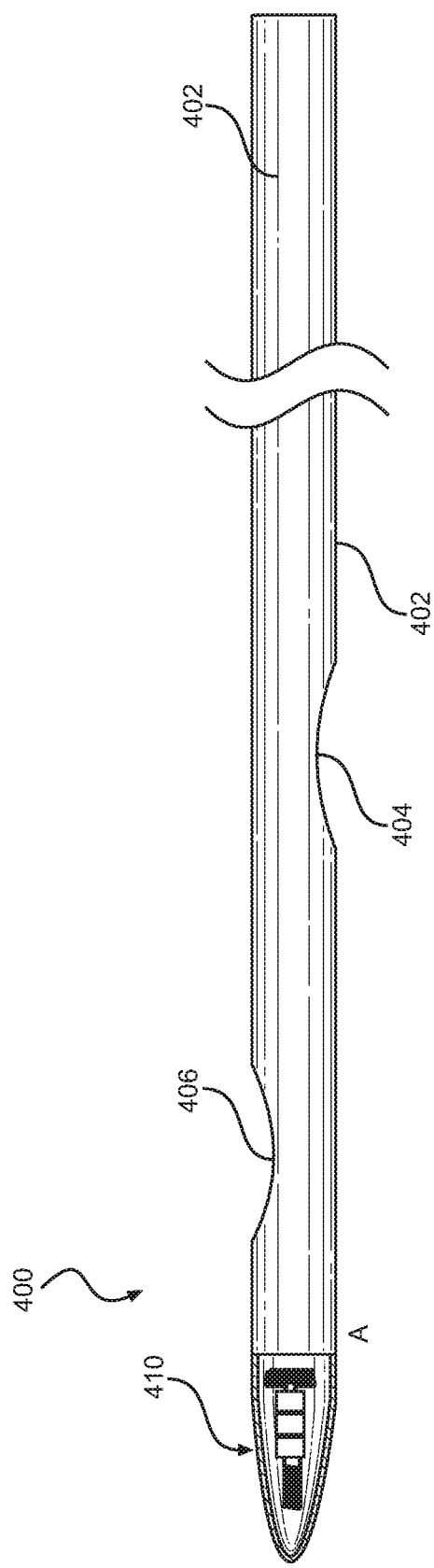
FIG. 5 depicts a perspective view of an example medical device such as a catheter according to aspects of the disclosure.
Figure 6:
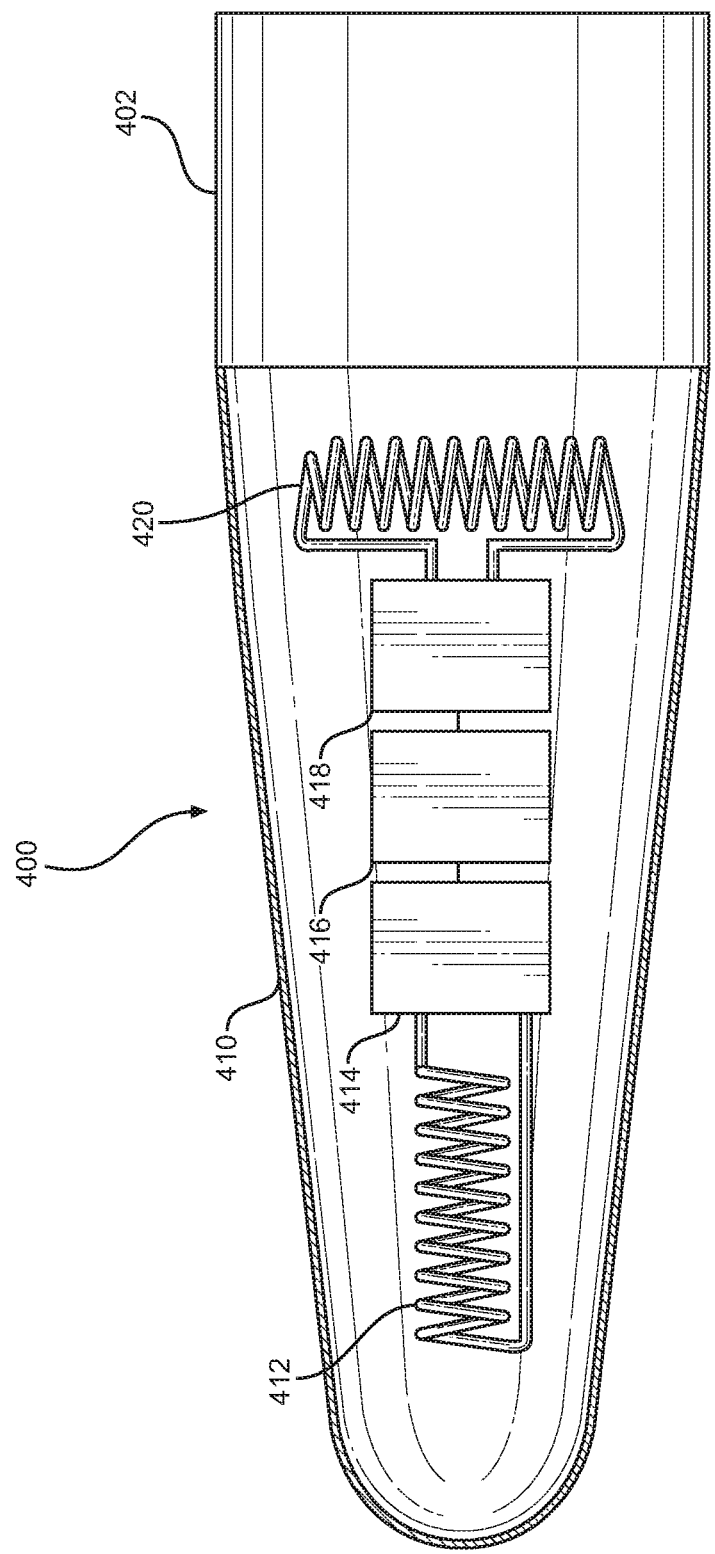
FIG. 6 depicts an enlarged view of a region A of the example medical device depicted in FIG. 5.
Figure 7:
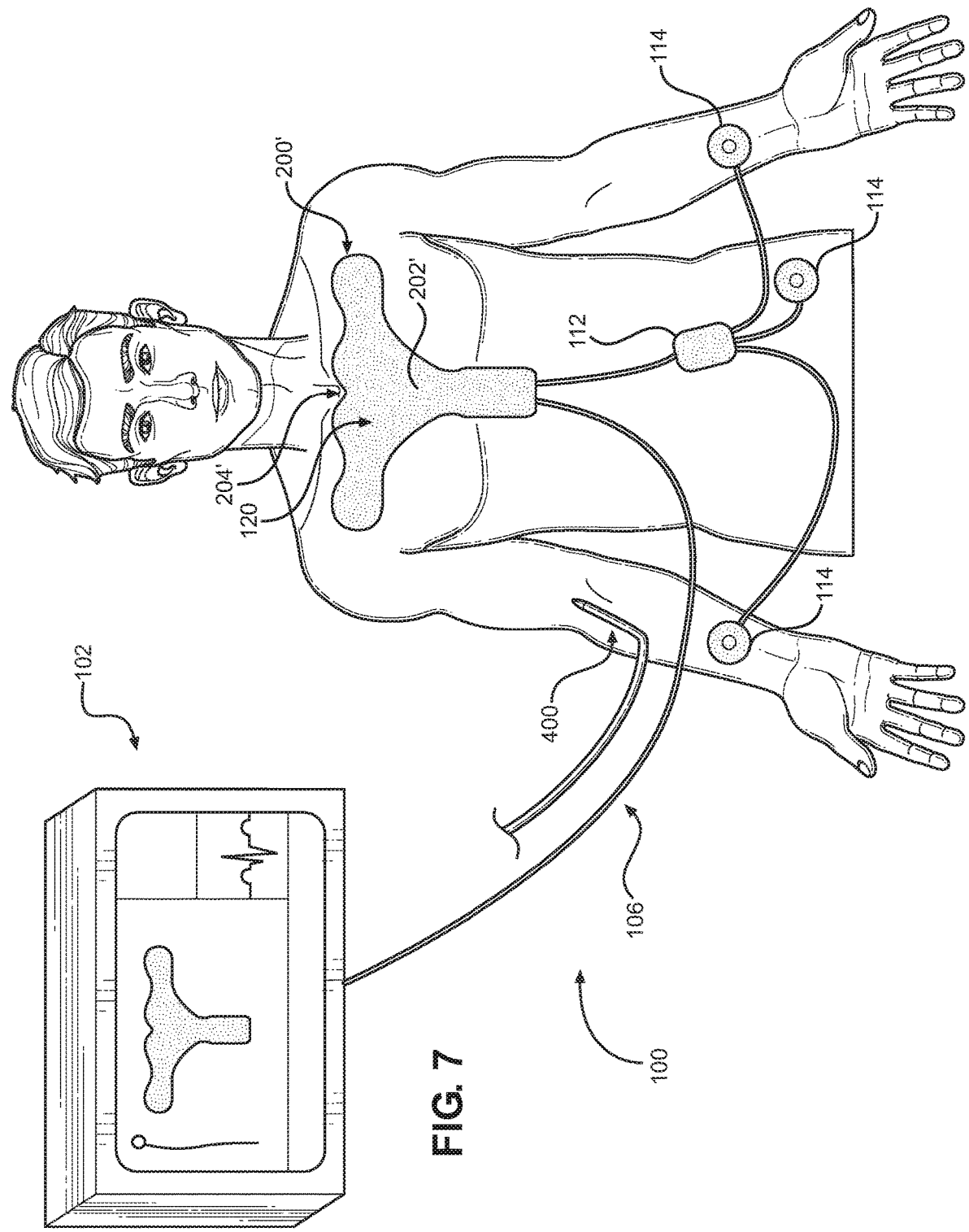
FIG. 7 depicts a schematic overview of a medical device navigation system positioned on a body of a patient according to aspects of the disclosure.

FIG. 1 depicts a schematic overview of an example medical device navigation system 100. The system 100 may include a computer console or control system 102 with a display 104. The display 104 may include a touchscreen configured to receive inputs from a physician or other user. The system 100 may also include an external unit such as a chest plate 200 and a catheter 400 as depicted in FIGS. 5-7. The chest plate 200 may be configured to be placed on the chest of a patient, and may be secured to the patient using adhesives or straps. The chest plate 200 may be connected to the system 100 via a wire or conductor 106, or the chest plate 200 may be connected to the system 100 via a wireless connection or network. Further details of the chest plate 200 are provided below in reference to FIG. 3.

The system 100 may also include an optional electrocardiogram (ECG) unit 112 having connections 116 to one or more ECG leads 114. The chest plate 200 may be connected to or in wireless communication to the ECG unit 112 wirelessly or via the wire or conductor 108, or the ECG unit 112 may be separately connected to the computer console 102. The ECG unit 112 may provide ECG measurements to the computer console 102 that may be used to assist in determining a position of a catheter or other medical device.

Figure 2:
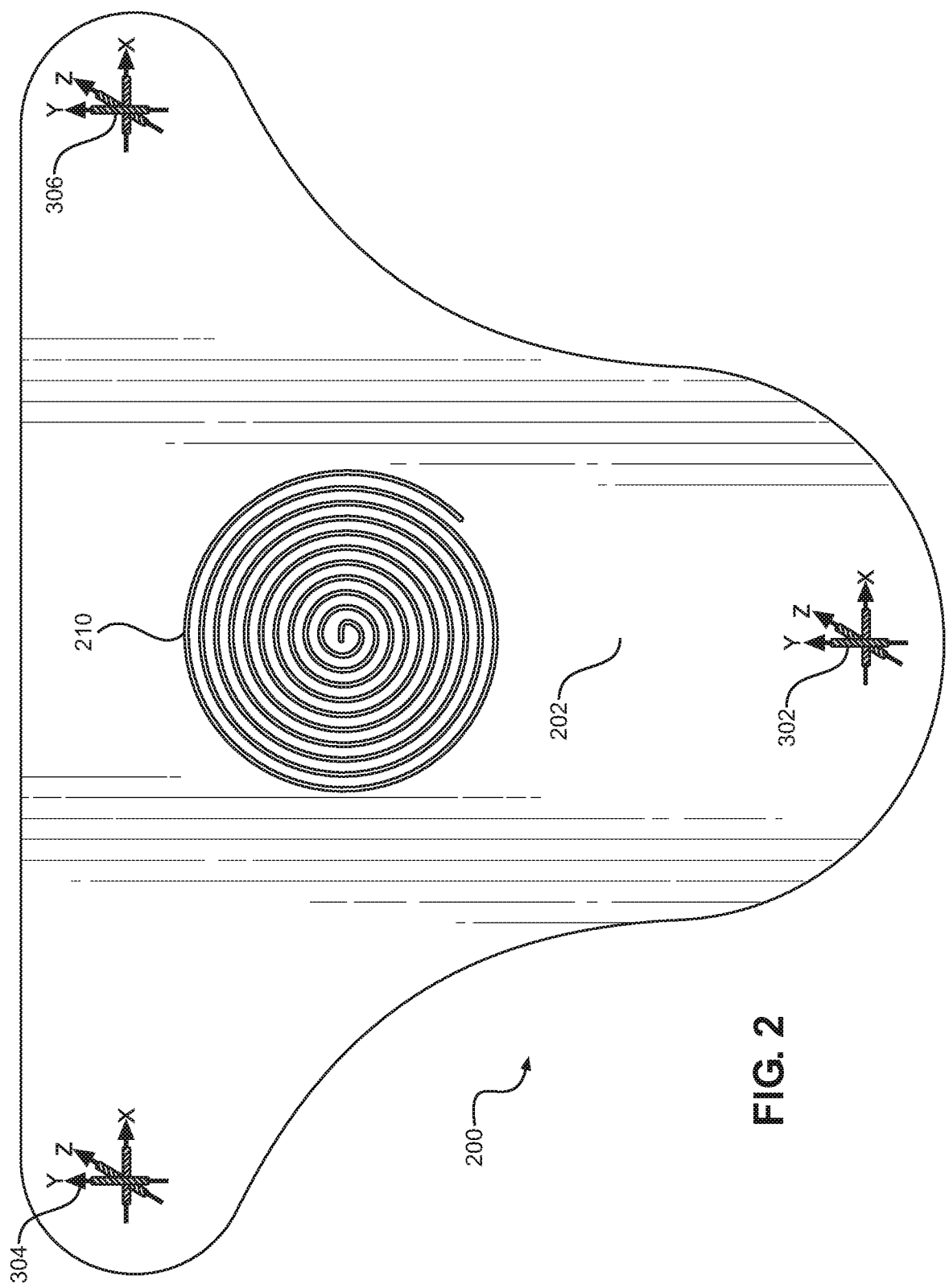
FIG. 2 depicts an example of an external power and sensing unit according to aspects of the disclosure.

FIG. 2 depicts an exemplary view of the chest plate 200. The chest plate 200 may be an extracorporeal assembly that is placed on a chest of the patient. According to different aspects of the disclosure, the chest plate 200 may include two or more sets of three-axis sensors (e.g., 302, 304, and 306) disposed on a body 202. Each three-axis sensor 302, 304, and 306 may include triple-axis antennas which receive a beacon transmission from an internal navigational antenna (e.g., antenna 412 depicted in FIG. 6 and described below). The triple-axis antennas may have three orthogonally arranged antennas, for example, a first antenna positioned along an axis X, a second antenna positioned along an axis Y, and a third antenna positioned along an axis Z. Each antenna may be configured to receive the beacon transmission from the internal navigational antenna. The body 202 may have a generally triangular configuration with the three-axis sensors 302, 304, 306 positioned on the corners and/or on the edge of the body 202. Alternative, the three-axis sensors 302, 304, 306 may be mounted as feet protruding from a bottom of the body 202.

The chest plate 200 may further include a coil or spiral antenna 210 disposed on the body 202. The spiral antenna 210 may be a radiating antenna that produces a RF or magnetic field in response to an alternating current being driven through the spiral antenna 210. Specifically, the computer console 102 may energize the spiral antenna 210 by driving an alternating current through the spiral antenna 210, which then creates a RF signal. The RF signal may induce a current and voltage in an internal harvesting antenna or coil (e.g., antenna 420 depicted in FIG. 6 and described below). According to certain aspects, the spiral antenna 210 may be a large Archimedean antenna. The spiral antenna 210 may be disposed in a center portion of the body 202. However, in some embodiments, one or more of the three-axis sensor 302, 304, and 306 and the spiral antenna 210 may be separate from the body 202, or the body 202 may be omitted.

Figure 4:
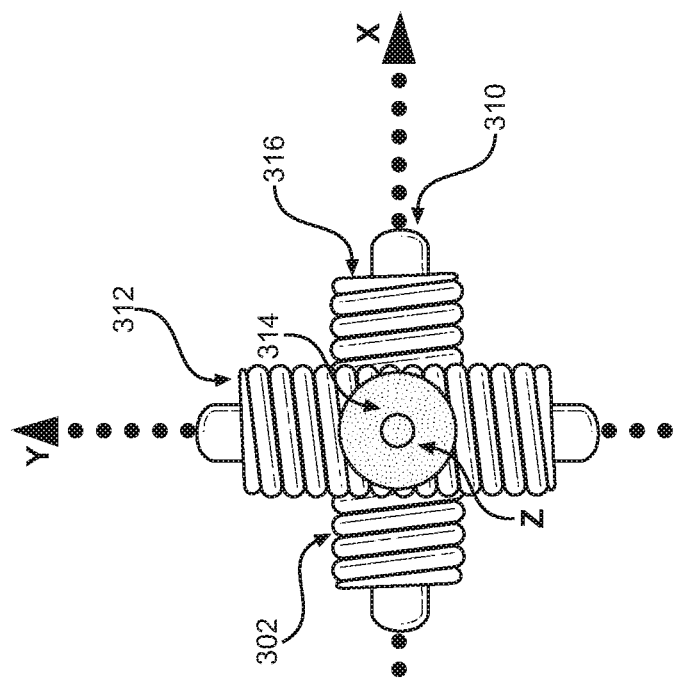
FIG. 4 depicts a second view of the example three-axis sensor depicted in FIG. 3.
Figure 3:
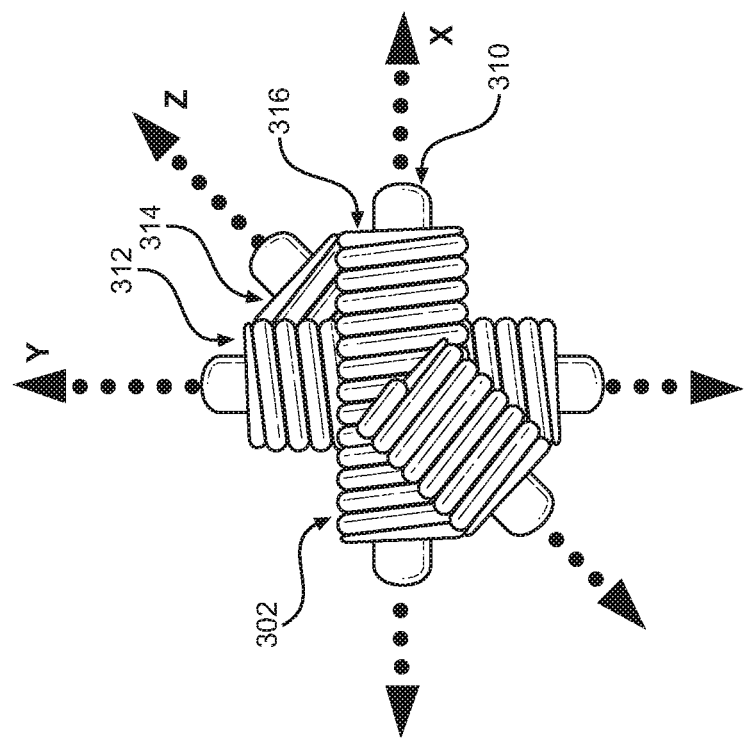
FIG. 3 depicts a first view of an example three-axis sensor having three orthogonally arranged receiver coils according to aspects of the disclosure.

FIGS. 3 and 4 depict different views of an exemplary three-axis sensor 302. As shown, the triple-axis sensor 302 may comprise three orthogonally arranged receiver coils, such as a X-coil 312, a Y-coil 314, and a Z-coil 316. Each of the X-coil 312, the Y-coil 314, and the Z-coil 316 may have a ferrite or ferrous core 310, or in an alternative arrangement, each of the X-coil 312, the Y-coil 314, and the Z-coil 316 may have an open air core. For example, each coil 312, 314, and 316 may include an insulated wire with a plurality of windings (e.g., 100 turns) around the ferrite or ferrous core 310. Each coil 312, 314, 316 may have a set of lead wires (not shown) to connect to the computer console 102.

In use, the coils 312, 314, 316 may be indexed to a specific anatomical landmark, such as the patient's sternal notch via a relative positioning on the chest plate 200, which itself is positioned or indexed to such an anatomical landmark, and may receive RF signals generated by the antenna 412. The coils 312, 314, and 316 may transmit the received RF signals to the computer console 102 for processing. The computer console 102 may use the received RF signals to calculate the position of the radiating antenna in three-dimensional space. The calculations may involve vector summing and adjustments using calibration values. As the catheter moves in the three-dimensional space and its position changes, the computer console 102 may join the different calculated positions to graphically display a trajectory or navigational path of the catheter, for example, on the display 104. Exemplary methods and systems, and other components, methods, or systems which may be incorporated in the present invention, including systems 100, is provided in U.S. Pat. Nos. 8,380,289 and 8,391,956, and U.S. Patent Application Publication Nos. 2016/0245766, 2016/0245670, and 2016/0320210, all of which are fully incorporated by reference herein.

FIG. 5 depicts a side view of an example medical instrument (e.g., a catheter 400). The catheter 400 may have a tubular body 402, one or more openings 404 and 406, and a tip 410. The catheter 400 may be configured to be inserted into a patient. The tubular body 402 may be flexible and have a proximal end and a distal end ending in the tip 410. A proximal end of the tip 410 may be attached to the distal end of the tubular body 402, and dimensions of the proximal end of the tip 410 may correspond to dimensions of the distal end of the tubular body 402 such that a seamless attachment is formed between the tubular body 402 and the tip 410 of the catheter 400. The tubular body 402 may have a lumen in fluid communication with the one or more openings 404, 406. The lumen and one or more openings 404, 406 may deliver a liquid medication to a specific location within the patient's vasculature after the catheter 400 is placed within the patient. The catheter 400 may be a cardiac catheter, CVC, or PICC.

FIG. 6 depicts an exemplary cross-sectional view of the tip region of the catheter 400. As shown, the tip 410 of the catheter 400 may be flexible, similar to the body of the catheter 400. The tip 410 may comprise a wireless energy harvesting and navigation system. The main components of the wireless energy harvesting and navigation system may be an energy harvesting coil or antenna 420, a rectification and filtration circuit 418 for harvesting DC power, a frequency generator or oscillator 416 for producing a navigational RF signal, a RF amplifier 414 for providing adequate power to the navigational RF signal, and a navigational antenna or beacon 412 which transmits the signal from the amplifier to sensors on an external unit (e.g., chest plate 200).

In an aspect, the harvesting coil or antenna 420 may be induced by the RF signal generated by the spiral antenna 210 to have an alternating current. This alternating current may be rectified and filtered by the rectification and filtration circuit 418, which uses it to produce a source of DC power. Although the rectification and filtration circuit 418 is depicted as a single element, it should be understood that the rectification and filtration circuit 418 includes a rectifier and a filter. The source of DC power may then be used to power the oscillator 416 to generate the navigational RF signal. The amplifier 414 may then amplify the navigational RF signal, and the amplified RF signal may be transmitted or broadcasted by the transmitting antenna or beacon 412. This transmitted RF signal may then be received and measured by the individual coils or antennas of the triple-axis sensors 302, 304, and 306.

FIG. 7 depicts an exemplary embodiment of the medical device navigation system 100 positioned on a body of a patient. As illustrated, the medical device navigation system may include the external computer console 102 connected to an external unit or chest plate 200' via the wire or conductor 106. The chest plate 200' may be similar to the chest plate 200 (described above), but may have a body 202' that includes a structure 204' for aligning with a sternal notch 120 of the patient. The chest plate 200' may be adapted to different shapes, configurations, or arrangements that may align with anatomical features (e.g., the sternum) of the patent. In alternative non-limiting embodiments, the sternal notch 120 may be adapted to be one or more of a notch, an extrusion, a marked portion, or an alignment hole. Alignment with the sternum may be a preferred location to place the chest plate 200' when monitoring and tracking the location of a catheter being inserted into the patient's vasculature near the patient's heart. In all other aspects, the chest plate 200' may be the same as the chest plate 200. For example, the chest plate 200' may also include a spiral antenna and three sets of triple-axis sensors. The chest plate 200' may also optionally be connected to an ECG unit 112 for measuring the patient's ECG signal.

As further illustrated, the catheter 400 may be inserted within the patient. The catheter 400 may be peripherally inserted (e.g., into an arm of the patient) and guided to the lower third of the patient's SVC. As the catheter nears the chest plate 200', the chest plate 200' may induce a current within the catheter 400 such that a navigational RF signal may be generated by the oscillator 416. In some embodiments, the system 100 may, additionally or alternatively, be implemented for use among a number of other insertion points, such as peripheral insertion (e.g., cephalic vein), midline insertion (e.g., basilic vein), central venous insertion (e.g., interjugular vein), chest insertion (e.g., subclavian vein or axillary vein) or groin (e.g., femoral vein). Moreover, in some embodiments, the system 100 may be used for placement or insertion sites for nephrostomy or kidney dialysis.

Figure 8:
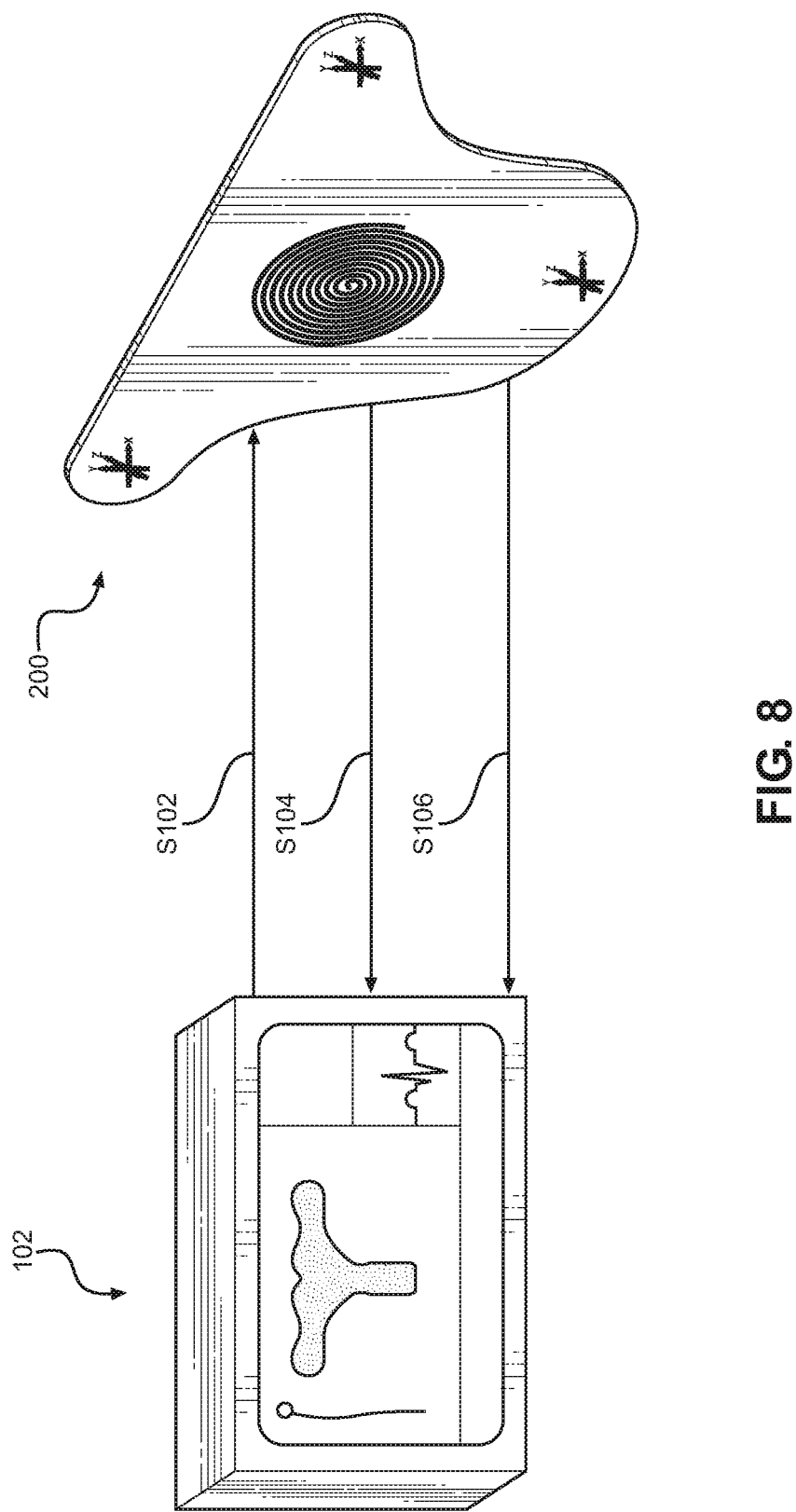
FIG. 8 depicts an example of signals that are communicated between various components of a medical device navigation system according to aspects of the disclosure.

FIG. 8 illustrates a schematic view of one or more signals being transmitted between the external computer console 102 and the external unit or chest plate 200. The computer console 102 may transmit a first signal S102 configured to power and energize the spiral antenna 210. As described above, such energizing of the spiral antenna may generate a first RF signal that is received by the harvesting antenna 420 disposed in the tip 410 of the catheter 400. The oscillator 416 of the catheter 400 may then generate a second RF signal, which can be amplified and transmitted and ultimately received and measured by the antennas of the triple-axis sensors 302, 304, and 306. The received and measured RF signals S104 may then be sent to the computer console 102 for additional processing, for example, to determine or calculate the position of the catheter 400 relative to the location of a portion of the chest plate 200. The chest plate 200 may also be connected to an ECG unit 112, which may provide measured ECG signals S106 that can also be sent from the chest plate 200 to the computer console 102.

Figure 9:
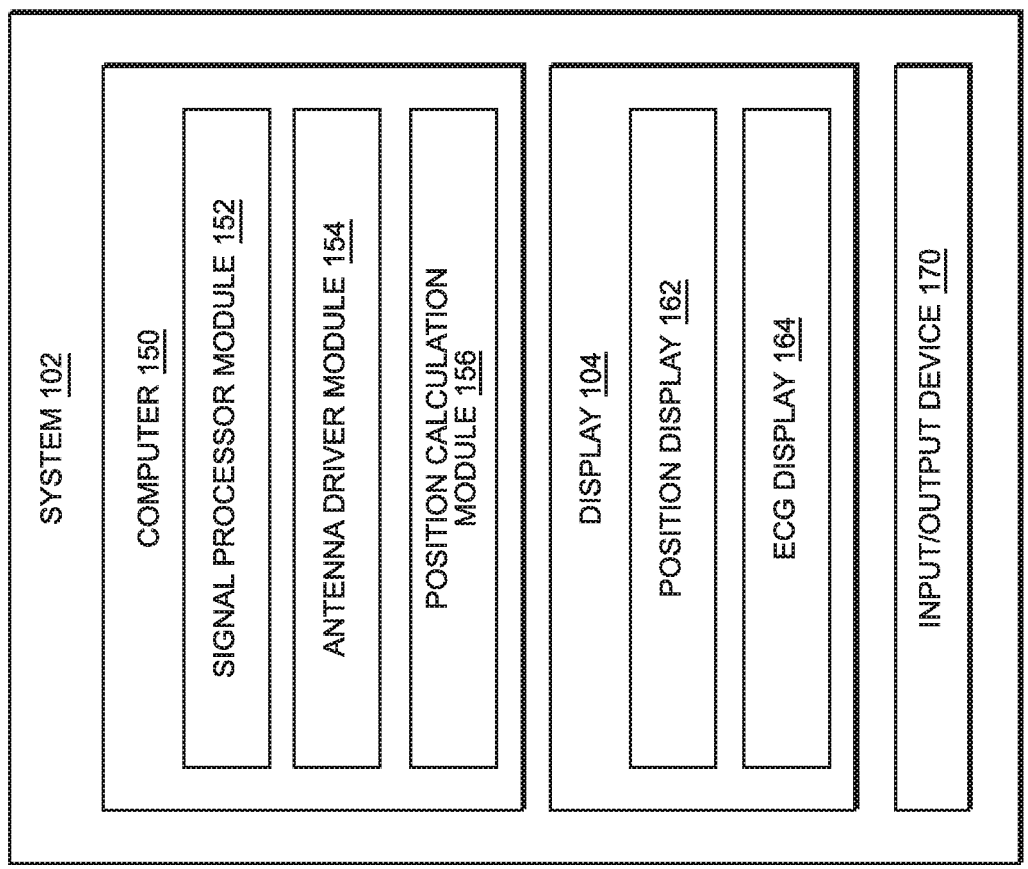
FIG. 9 depicts a schematic diagram of a computer system used in a medical device navigation system according to aspects of the disclosure.

The computer console or control system 102, as schematically depicted in FIG. 9, may include a processor or computer 150. The computer 150 may have a signal processor module 152 that processes one or more of the signals S104, S106 received from the chest plate 200, an antenna driver module 154 configured to control and power the spiral antenna 210 of the chest plate 200, and a position calculating module 156 configured to receive the signals S102 and S104 and calculate the position of the catheter 400. The position calculating module 156 may calculate the position of the catheter 400 by using known algorithmic vector summing methods, as detailed above.

The computer console 102 may also include a display 104, which, as described above, may include a touchscreen. The display 104 may have a position display 162 which displays a position of the catheter 400 relative to the chest plate 200, and a ECG display 164 which displays a measured ECG signal (e.g., the ECG signal measured by the ECG unit 112) of the patient. The computer console 102 may also include an input/output device 170, which sends signals to and receives signals from the chest plate 200.

The many features and advantages of the medical device navigation systems described herein are apparent from the detailed specification, and thus, the claims cover all such features and advantages within the scope of this application. Further, numerous modifications and variations are possible. As such, it is not desired to limit the medical device navigation systems to the exact construction and operation described and illustrated and, accordingly, all suitable modifications and equivalents may fall within the scope of the claims.

What is claimed is:

1. A navigation system for placing a medical device into a patient, the system comprising:
    an external unit configured to be disposed on a chest of the patient, the external unit comprising:
        a radiating element configured to produce a first radio frequency ("RF") signal; and
        a plurality of three-axis sensors, each three-axis sensor comprising three receiver coils configured to receive a second RF signal;
    a control system connected to the external unit; and
    the medical device comprising:
        a first antenna configured to receive the first RF signal and supply power to a second antenna; and
        the second antenna configured to broadcast a second RF signal such that the receiver coils of the plurality of three-axis sensors receive the second RF signal,
    wherein the control system is configured to energize the radiating element, and the radiating element produces the first RF signal when the control system energizes the radiating element, and
    wherein the control system is configured to determine a position of the second antenna relative to the external unit based on the second RF signal received by the receiver coils of the plurality of three-axis sensors.

2. The navigation system of claim 1, wherein the first antenna is configured to produce an alternating current, and the medical device further comprises:
    a rectifier configured to convert the alternating current into a direct current; and
    a frequency generator configured to produce the second RF signal,
    wherein at least the frequency generator and the second antenna are energized by the direct current.

3. The navigation system of claim 2, wherein the medical device further comprises a filter configured to filter the alternating current.

4. The navigation system of claim 1, wherein the medical device further comprises an amplifier configured to amplify the second RF signal.

5. The navigation system of claim 1, wherein the first RF signal has a different frequency than the second RF signal.

6. The navigation system of claim 1, wherein the external unit comprises a plate having a generally triangular configuration.

7. The navigation system of claim 6, wherein the radiating element is disposed in a center portion of the plate.

8. The navigation system of claim 7, wherein the plurality of three-axis sensors comprises three three-axis sensors, each of the three three-axis sensors being disposed proximate to an outer edge of the plate.

9. The navigation system of claim 1, wherein the radiating element comprises an Archimedean spiral antenna.

10. The navigation system of claim 1, wherein the receiver coils comprise an insulated wire wound around a core wire.

11. The navigation system of claim 1, wherein the medical device comprises a proximal portion and a distal portion, the distal portion of the medical device configured to be disposed in the patient, and at least the second antenna is disposed in the distal portion of the medical device.

12. The navigation system of claim 11, wherein the first antenna is disposed in the distal portion of the medical device.

13. The navigation system of claim 1, wherein the medical device is a catheter.

14. A catheter configured to be inserted into a patient, the catheter comprising:
a flexible tubular body having a proximal end and a distal end; and
a tip attached to the distal end of the flexible tubular body, the tip comprising:
a first antenna configured to receive a first radio frequency ("RF") signal and produce an alternating current;
a filter configured to filter the alternating current;
a rectifier configured to convert the filtered alternating current into a direct current;
a frequency generator configured to produce a second RF signal;
an amplifier configured to amplify the second RF signal; and
a second antenna configured to broadcast the second RF signal,
wherein at least the frequency generator, the amplifier, and the second antenna are energized by the direct current.

15. The catheter of claim 14, wherein the flexible tubular body comprises a lumen extending from the proximal end to the distal end, and the lumen is in fluid communication with one or more openings disposed proximate to the distal end of the flexible tubular body.

16. The catheter of claim 14, wherein the catheter is configured to deliver a fluid to a location within the patient.

17. The catheter of claim 14, wherein a tip of the catheter has a tapered surface.

18. The catheter of claim 17, wherein the tip of the catheter has a conical configuration.

19. The catheter of claim 17, wherein a proximal end of the tip is attached to the distal end of the flexible tubular body, and proximal end of the tip has dimensions corresponding to dimensions of the distal end of the flexible tubular body such that a seamless attachment is formed between the flexible tubular body and the tip of the catheter.

20. A chest plate configured to be disposed on a chest of a patient, the chest plate comprising:
a radiating element configured to produce a first radio frequency ("RF") signal;
and
a plurality of three-axis sensors, each three-axis sensor comprising three receiver coils configured to receive a second RF signal,
wherein the radiating element is disposed in a center portion of the chest plate,
and
wherein each of the plurality of three-axis sensors is disposed proximate to an outer edge of the chest plate.

* * * * *